(12) United States Patent
Zhang

(10) Patent No.: US 8,666,483 B2
(45) Date of Patent: Mar. 4, 2014

(54) SYSTEM FOR CARDIAC MEDICAL CONDITION DETECTION AND CHARACTERIZATION

(75) Inventor: Hongxuan Zhang, Schaumburg, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1119 days.

(21) Appl. No.: 12/250,141

(22) Filed: Oct. 13, 2008

(65) Prior Publication Data

US 2009/0112110 A1   Apr. 30, 2009

Related U.S. Application Data

(60) Provisional application No. 60/982,249, filed on Oct. 24, 2007.

(51) Int. Cl.
*A61B 5/00* (2006.01)
(52) U.S. Cl.
USPC .......................................................... 600/518
(58) Field of Classification Search
USPC .................................................. 600/508–523
See application file for complete search history.

(56) References Cited

U.S. PATENT DOCUMENTS

| | | | |
|---|---|---|---|
| 5,782,876 A | 7/1998 | Flammang | |
| 6,490,479 B2 | 12/2002 | Bock | |
| 6,889,080 B2 * | 5/2005 | Henry et al. | 607/14 |
| 7,314,446 B2 | 1/2008 | Byrd et al. | |
| 2003/0163057 A1 * | 8/2003 | Flick et al. | 600/509 |
| 2007/0032733 A1 * | 2/2007 | Burton | 600/509 |
| 2008/0086177 A1 * | 4/2008 | Min et al. | 607/25 |
| 2008/0167567 A1 * | 7/2008 | Bashour et al. | 600/518 |

FOREIGN PATENT DOCUMENTS

WO   WO 2008/007236   1/2008

* cited by examiner

*Primary Examiner* — Scott Getzow
(74) *Attorney, Agent, or Firm* — Brennan K Bradley

(57) ABSTRACT

A system and method provides monitoring for atrial fibrillation. A data acquisition processor acquires a cardiac signal data stream from a patient and a wave detector detects an R-wave in a cardiac signal of the data stream. A T-wave in the cardiac signal occurring after the detected R-wave and a Q-wave in a subsequent cardiac signal of the data stream is also detected by the wave detector. A filter provides signal gating and extraction of data representing a Region of Interest (ROI) time window from the detected T-wave to the Q-wave. An integration processor detects characteristics of a P wave signal occurring within the ROI time window. At least one of the detected P wave characteristics is compared to characteristics derived from data representing at least one P wave signal and generating an output signal in response to the comparison for use in determining if the patient is in atrial fibrillation.

21 Claims, 6 Drawing Sheets

Windowed signal processing for atrial arrhythmia

Electrophysiological signal in the ROI

Healthy beat    AF beat

1. RR wave interval, HRV, statistical analysis

2. Multi-heart beat (window of ROI) averaging

3. P wave amplitude and latency analysis

4. Single/multi P wave Max-min analysis
   (Peak number and duration)

5. Energy integration of ROI window

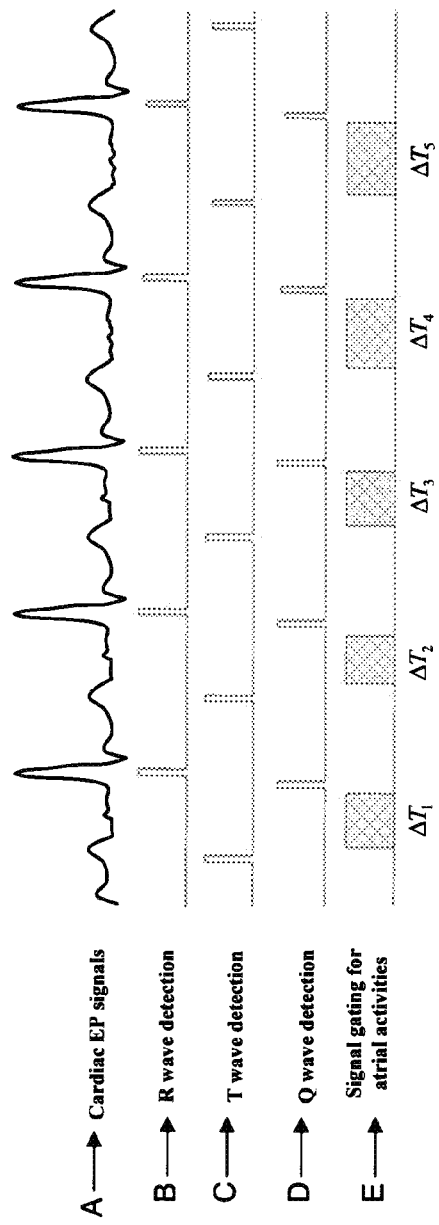
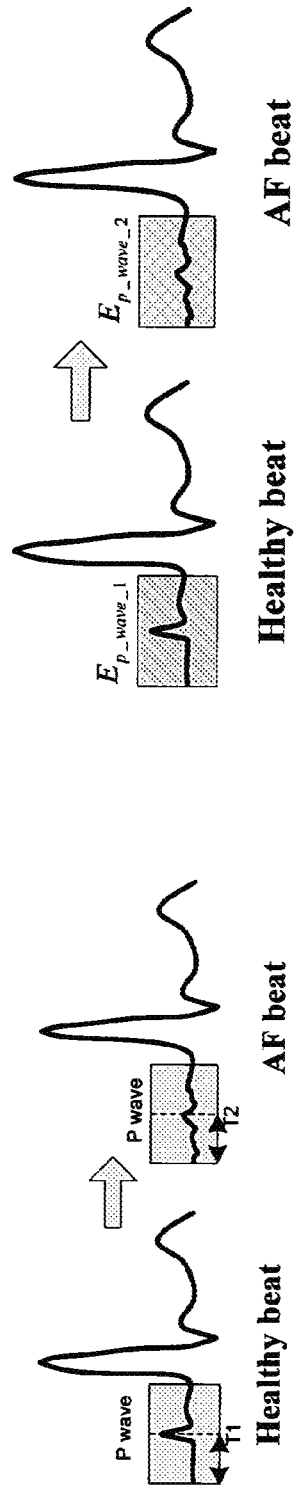
Fig. 4
Fig. 5
Fig. 6

SYSTEM FOR CARDIAC MEDICAL CONDITION DETECTION AND CHARACTERIZATION

This is a non-provisional application of provisional application Ser. No. 60/982,249 filed Oct. 24, 2007, by H. Zhang et al.

FIELD OF THE INVENTION

This invention concerns a system and method for analyzing cardiac electrophysiological signals (including Electrocardiograms (ECG's) and internal cardiac electrograms) based on signal gating techniques and windowed atrial electrophysiological activity analysis to provide data used in identifying cardiac disorders, differentiating cardiac arrhythmias, characterizing pathological severities and prediction of life-threatening events, for example.

BACKGROUND OF THE INVENTION

Atrial fibrillation (AF) is the most common abnormal heart rhythm, especially in seniors, with irregular and erratic cardiac patterns. Usually, surface ECG signal analysis based on waveform morphology and time domain parameters are utilized for cardiac AF rhythm detection and characterization, such as P wave morphology changes, R-R-wave time interval, heart rate variability analysis, etc. However, the waveform morphologies and time domain parameter analysis are sometimes subjective and time-consuming, and require extensive expertise and clinical experience for accurate pathology interpretation and proper cardiac rhythm management. Some sophisticated mathematical theories have been applied to biomedical signal interpretation, for example, frequency analysis (such as dominant frequency analysis, frequency singularity, etc), wavelet decomposition analysis, statistical analysis (such as autocorrelation analysis, coherence analysis, etc), and nonlinear entropy evaluation. Nevertheless, these applications focus on generating a new pathology index for qualitative cardiac AF rhythm identification. Until now no well-accepted methods and algorithms for qualitative and quantitative characterizing AF, especially the severity quantification of AF pathology, have been developed. Several shortcomings with current clinical investigation and diagnosis strategies for atrial fibrillation exist. For example:

1. Clinical real time and accurate AF diagnosis and characterization need extensive clinical experience and medial expertise for precise and correct cardiac electrophysiological signal interpretation. This usually increases the clinical training cost and the complexity involved in diagnosing a condition.
2. Time domain parameter based analysis, such as R-R-wave interval and heart rate variability (HRV), is utilized for qualitative diagnosis and detection of AF. However, these methods do not accurately characterize the pathological severity of the AF pathology.
3. Clinically, most AF diagnosis and evaluation are based on the whole heart beat. This includes P wave, QRS complex T-wave, etc. analysis. Some analysis and filtering algorithms (frequency analysis) employ the whole heart beat for AF malfunction pattern recognition and characterization. This unavoidably increases the risk of signal/analysis distortion caused by noise and artifacts.
4. Algorithm simplicity, accuracy and ease of use are hurdles that need to be overcome with current AF analysis and characterization. For example heart rate variability is utilized for AF recognition. However, there are extensive statistical evaluations on the variability threshold which may be different from patient to patient. These kinds of medical diagnosis factors may present more application complexities to the user. Furthermore, some of current AF research methods and applications are not stable, time consuming and have a high error rate (false alarm risk).

The need exists for more reliably and precisely identifying the cardiac disorders, differentiating cardiac arrhythmias, characterizing the pathological severities, and even prediction of the life-threatening events. A system according to invention principles addresses these deficiencies and related problems.

SUMMARY OF THE INVENTION

A system provides monitoring and analysis of ECG signals by evaluating the P wave of the signal. A system monitors atrial fibrillation by analyzing a cardiac signal acquired by a data acquisition processor. The data acquisition processor acquires a cardiac signal data stream from a patient. A wave detector detects an R-wave in a cardiac signal of the data stream. The wave detector then detects a T-wave in the cardiac signal occurring after the detected R-wave and a Q-wave in a subsequent cardiac signal of the data stream. A filter provides signal gating and extraction of data representing a Region of Interest (ROI) time window from the detected T-wave to the Q-wave. An integration processor detects characteristics of a P wave signal occurring within the ROI time window. At least one of the detected P wave characteristics is compared to characteristics derived from data representing at least one P wave signal and an output signal is generated in response to the comparison for use in determining if the patient is in atrial fibrillation.

BRIEF DESCRIPTION OF THE DRAWING

FIGS. 4a-4e show a cardiac electrophysiological signal and signal gating and Region of interest window extraction strategies, according to invention principles.
FIG. 5 shows a comparison of amplitude and latency P wave analysis for a healthy heart beat and an arterial fibrillation heart beat, according to invention principles.
FIG. 6 shows a comparison of energy/entropy for a healthy heart beat and an arterial fibrillation heart beat, according to invention principles.

DETAILED DESCRIPTION OF THE INVENTION

Figure 1:
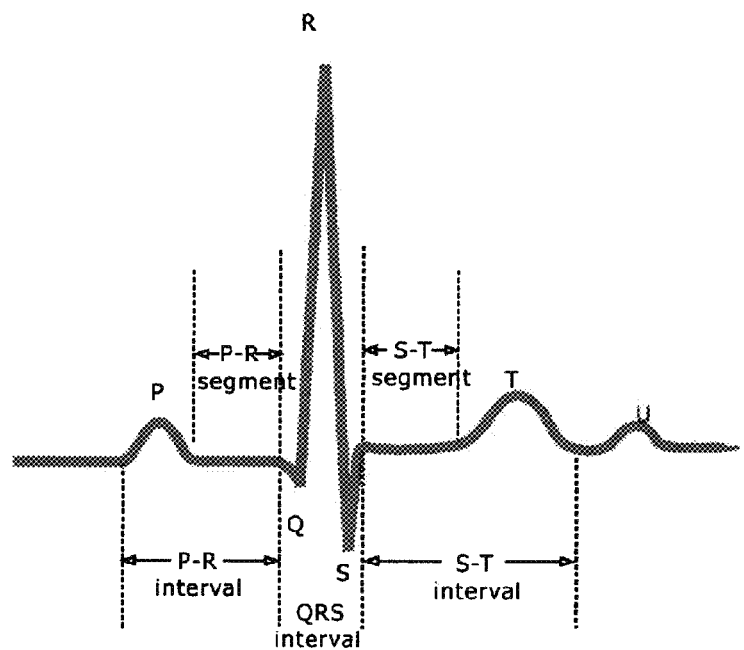
FIG. 1 shows a typical one-cycle ECG tracing.

A medical electrophysiological signal analysis system provides improved signal/noise ratio (SNR) and accuracy. A method according to invention principles analyzes cardiac electrophysiological signals (including ECG and internal cardiac electrograms) based on signal gating techniques and windowed atrial electrophysiological activity analysis. The system advantageously provides a stable, accurate, and efficient method and strategy for monitoring and diagnosing cardiac arrhythmia, especially atrial fibrillation. The signal gating and windowed signal processing based cardiac pathology and malfunction diagnosis and characterization provide a precise approach for identifying cardiac disorders, predicting the cardiac pathology occurrence, and diagnosis of cardiac malfunction characteristics. This provides better input with medical decision and clinical treatment, such as drug delivery and long term cardiac care. The system provides the following features:

Signal gating achieved in real time cardiac signal monitoring, recording and analyzing. A signal gating system uses multi synchronization signals to extract the electrophysiological signals and activities of the atrium. For example, from the end of a T-wave to the beginning of a QRS complex. The precision of atrial signal capture greatly improves the accuracy of the atrial pathology analysis.

Signal gating system and windowed atrial electrophysiological activity analysis may employ microcontroller and DSP calculations, for example. This technology is utilized for automatic online analysis and detection of atrial fibrillation and hence provides more convenient and reliable data analysis results to clinical doctors, qualitatively (arrhythmia type) and quantitatively (arrhythmia severity).

The gating system facilitates precise extraction of an atrial activities portion (Region of Interest (ROI)) and windowed signal analysis combines the heart activity averaging (HRV), filtering and quantitative calculations for AF capture and characterization. The methods and strategies according to invention principles provide more stable and reliable diagnosis and accurate pathology feedback to clinical doctors in the presence of bio-noise and electrical artifacts.

The adaptive AF pathology analysis in the system utilizes both cardiac signal amplitude (P wave voltage potentials) and time/latency (distance/duration from P wave to Q-wave) for monitoring and calculating atrial electrophysiological activity, which improves capturing atrial arrhythmias, such as atrial flutter and AV block, with better noise immunity.

The analysis, strategy and diagnosis method according to invention principles is applied to both surface ECG signals and intra-cardiac electrograms, unipolar and bipolar.

The AF diagnosis methods according to invention principles requires low computation power and is able to be accomplished in the portable cardiac monitoring and function devices, such as an implantable cardiac device, pacemaker and cardioverter.

The signal gating system and windowed atrial electrophysiological activity analysis predicts AF arrhythmia during cardiosurgical operations, even drug administrations.

The signal gating system and windowed signal analysis for AF analysis and characterization is extended to analyzing other portions of the cardiac electrophysiological signals and activities. The system monitors and diagnoses the pathologies and malfunctions of the heart and cardiac circulation system during other cardiac arrhythmias, such as cardiac arrhythmia analysis and discrimination of different cardiac pathological rhythms, for example, atrial tachycardia and ventricle arrhythmias.

Certain embodiments employ arrhythmia analysis and signal gating for atrial electrophysiological activities and windowed cardiac signal analysis for AF detection and characterization.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by a user interface processor and enabling user interaction with a processor or other device and associated data acquisition and processing functions. The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

FIG. 1 illustrates a typical one-cycle ECG trace. The electrocardiogram (ECG) is a system of recording bioelectric currents generated by the heart. Clinicians use the ECG to evaluate the condition of a patient's heart and perform further diagnosis. An ECG tracing is obtained by sampling bioelectric currents sensed by several electrodes, known as leads. The electrocardiogram (ECG) is a time-varying signal reflecting the ionic current flow which causes the cardiac muscles to contract and relax. A surface ECG is obtained by recording the potential difference between two electrodes placed on the surface of the skin. A single normal cycle of the ECG represents the successive atrial depolarization/repolarization and ventricular depolarization/repolarization which occurs with each heart beat. These are approximately associated with the peaks and troughs of the ECG waveform as shown in FIG. 1. A typical ECG tracing of a normal heartbeat (or cardiac cycle) consists of a P wave, a QRS interval and a T-wave. A small U wave is normally visible in 50 to 75% of ECGs. The baseline voltage of the electrocardiogram is known as the isoelectric line, measured as the portion of the ECG tracing following the T-wave and preceding the next P wave.

During normal atrial depolarization, the main electrical vector spreads from the right atrium to the left atrium. This is identified as the P wave on the ECG. The QRS interval corresponds to the depolarization of the ventricles. Because the ventricles contain more muscle mass than the atria, the QRS interval is larger than the P wave. In addition, the QRS interval tends to look "spiked" rather than rounded due to the increase in conduction velocity. A normal QRS interval is 0.06 to 0.10 sec (60 to 100 ms) in duration, but any abnormality of conduction takes longer, and causes widened QRS intervals. The PR interval is measured from the beginning of the P wave to the beginning of the QRS interval, usually 120 to 200 ms in duration. When a Q-wave is measured with an ECG, the PR interval may be called the PQ interval instead. The ST segment connects the QRS interval and the T-wave and has a duration of 0.08 to 0.12 sec (80 to 120 ms). The ST segment starts at the end of the QRS interval and ends at the beginning of the T-wave. However, since it is usually difficult to determine exactly where the ST segment ends and the T-wave begins, the relationship between the ST segment and T-wave should be examined together (ST interval). The typical ST segment duration is usually around 0.08 sec (80 ms). It should be essentially level with the PR segment. The T-wave represents the repolarization (or recovery) of the ventricles. The interval from the beginning of the QRS interval to the apex of the T-wave is referred to as the absolute refractory period. The last half of the T-wave is referred to as the relative refractory period (or vulnerable period).

Extracting useful clinical information from the real (noisy) ECG requires reliable signal processing systems. Conventional systems include R-peak detection, QT-interval detection and the derivation of heart rate and respiration rate from the ECG. The RR-interval is the time between successive R-peaks, the inverse of this time interval gives the instantaneous heart rate. A series of RR-intervals is known as a RR tachogram and variability of these RR-intervals reveals important information about the physiological state of the subject.

Figure 2:
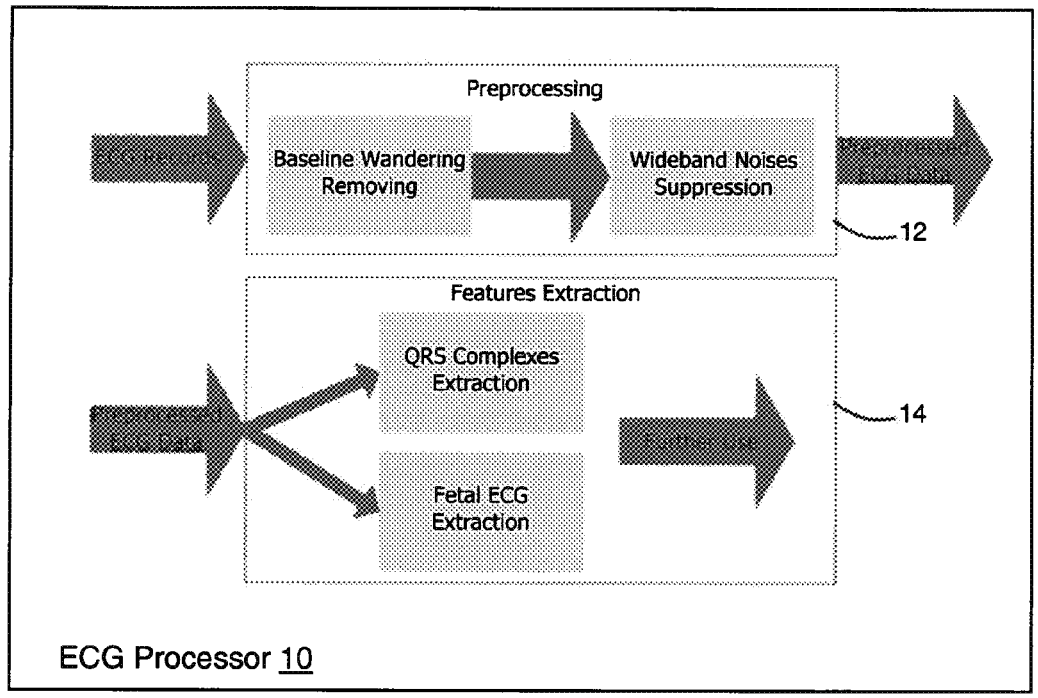
FIG. 2 shows a system for ECG signal extraction.

The recorded ECG signal is contaminated by noise and artifacts that is within the frequency band of interest and manifest with similar characteristics as the ECG signal itself. FIG. 2 provides an exemplary ECG processing system used in obtaining and producing measurable ECG signal data. In order to extract useful information from the noisy ECG signals, the raw ECG signals are processed in an ECG processor 10. ECG signal processing employs a preprocessing stage 12 and a feature extraction stage 14 as shown in FIG. 2. The preprocessing stage 12 removes or suppresses noise from the raw ECG signal and the feature extraction stage 14 extracts diagnostic information such as power line interference, electrode pop or contact noise, patient-electrode motion artifacts, electromyographic (EMG) noise and baseline wandering from the ECG signals. Among these noises, the power line interference and the baseline wandering are the most significant and can strongly affect ECG signal analysis. The electrocardiogram (ECG) is a time-varying signal reflecting the ionic current flow which causes the cardiac fibers to contract and subsequently relax. The surface ECG is obtained by recording the potential difference between two electrodes placed on the surface of the skin. A single normal cycle of the ECG represents the successive atrial depolarization/repolarization and ventricular depolarization/repolarization which occurs with each heart beat.

Figure 3:
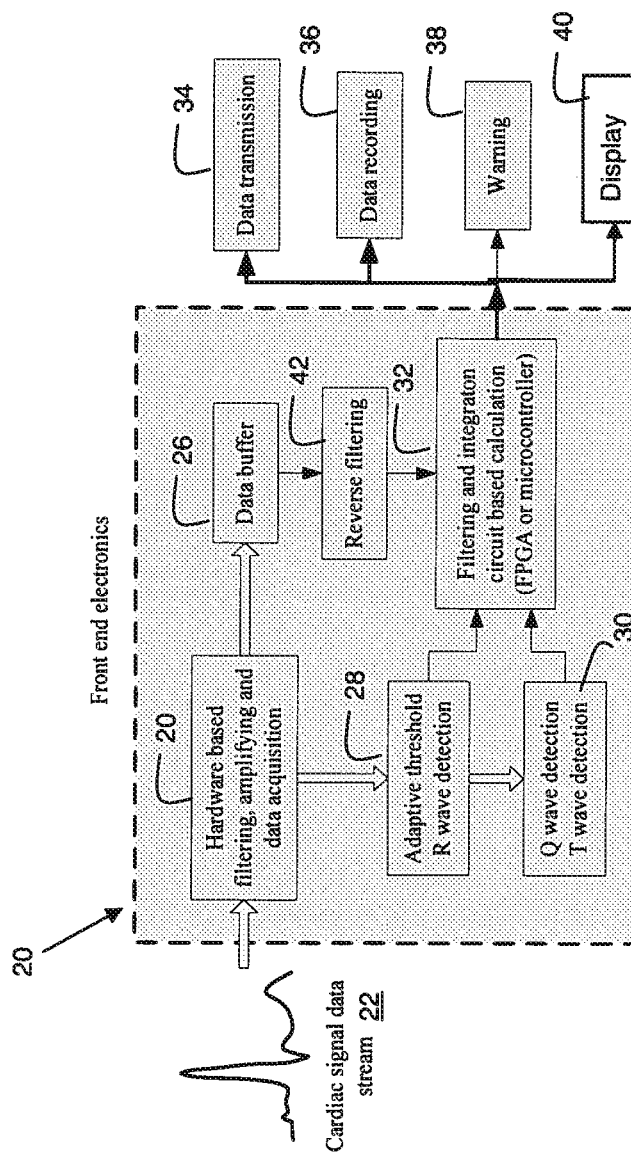
FIG. 3 shows a system for Atrial Fibrillation monitoring, according to invention principles.

FIG. 3 is a block diagram showing a system for monitoring, diagnosing and characterizing AF according to invention principles. The system uses signal gating and window analysis for AF data acquisition, diagnosis, characterization and warning generation. A cardiac signal data stream 22 is received by the system 20 and is provided to filtering, amplification and data acquisition circuitry 24. An example of such circuitry is shown and described above with respect to FIG. 2. The filtered and amplified cardiac signal data stream as shown in FIG. 4a is provided from the data acquisition circuitry 24 to a data buffer 26 as well as to both an R-wave detector 28 and a T and Q wave detector 30. The R-wave detector 28 uses adaptive threshold detection on the received cardiac signal data stream to perform the R-wave peak detection. The R-wave has a larger amplitude than any other portion of the cardiac signal data stream. A threshold signal between the normal peak of the R-wave and any other portion of the cardiac signal data stream may be selected for comparison with the cardiac signal data stream to detect the R-wave peak. Detection of the R-wave is depicted in FIG. 4b. The R-wave detector 28 transmits a signal to the T and Q wave detector 30 upon detection of an R-wave. After detection of the R-wave, the next peak of the cardiac signal data stream is the T-wave. Detection of the T-wave in each cardiac signal data stream is illustrated in FIG. 4c. The cardiac signal data stream is provided to the T and Q-wave detector 30 for detecting the next peak (T-wave) after detection of the R-wave. Once the T-wave is detected, the T and Q wave detector 30 senses for a minimum in the cardiac signal data stream. The minimum in the cardiac signal data stream represents the Q-wave of a subsequent signal as illustrated in FIG. 4d. Once the T and Q-waves are detected, a filter and integration circuit 32 uses the detected cardiac signal waveform peaks to detect the ROI portion gating, identification and extraction, such as P wave, Q-wave, R-wave, etc. The data buffer 26 provides the buffered cardiac signal data stream to a reverse filter 42. The reverse filter 42 filters the cardiac signal data stream in a reverse time sequence. The change in filtering direction reduces any phase distortion thus improving the signal quality. Through the synchronization of the T-wave and Q-wave (with some time adjustment), the atrial activities ROI window series (the T-Q window) is derived, $\Delta T_i$, for analysis purposes as identified in FIG. 4e.

Signal gating systems and windowed analysis are applied to the detected T-Q interval to detect characteristics of the signal. The signal gating systems and windowed analysis include determining an amplitude and latency of the P-wave within the T-Q interval as well as determining an energy or entropy of the P-wave within the T-Q interval. The amplitude is determined by measuring the area under the signal within the window. The latency of the P-wave indicates the position within the window at which the P-wave is detected. For amplitude and latency analysis, these characteristics are compared with characteristics derived from data representing at least one P wave signal and generating an output signal in response to the comparison for use in determining if the patient is in atrial fibrillation.

A comparison of amplitude and latency for a healthy heart beat and an AF beat is shown in FIG. 5. FIG. 5 identifies the T-Q window encompassing the P wave therein for both the healthy beat and the AF beat. The amplitude of each P wave is measured as shown by the dashed line and the latency, the time within each window that the P wave occurs, is identified by $T_1$ and $T_2$. The latency measures the distance of the P wave from both the T-wave and the Q-wave within the window. At the early stage of atrial arrhythmia, such as AF, the pathological changes within the electrophysiological activities of a P wave portion (windowed ROI signal) are not significant and may not be easily captured or detected by a clinical user. Extensive clinical expertise and knowledge of atrial arrhythmias is also required to detect the pathological changes. However, with the gated windowed ROI signal (P wave portion), computer based signal processing can readily capture the P wave amplitude and latency change, to 10 uV and 10 mS, for example. Amplitude and latency changes of the P wave are utilized as a reliable and sensitive measure for atrial fibrillation detection, diagnosis and especially the severity of the AF stages.

P wave latency may be determined according to the following formula:

$$\overline{\Delta T} = \sum_N \Delta T_i$$

In which, N is the number of P wave windows for averaging. Variability (variance, S) of the P wave time duration between ECG signals may be determined according to the following formula:

$$S = \sqrt{\sum_{i=1}^{N} (\Delta T_i - \overline{\Delta T})/(N-1)}$$

In which, N is the data sample number for variability calculation, (for example N=10); $\Delta T_i$ is the size of the P wave duration windows. The statistical analysis in the preferred embodiment is utilized adaptively for real time diagnosis and AF characterization.

The averaging time duration and variability are utilized as a signature of the P wave/atrial activities and some further statistical application may be used for the analysis and characterization of the severities of the AF pathology, such as high order statistics (HOS). At the same time, the detection threshold of the analysis index may be decided and adjusted based on the noise level, patients and heart/pacing rate.

A comparison of energy or entropy calculation for a healthy heart beat and an AF beat is shown in FIG. 6. FIG. 6 identifies the T-Q window encompassing the P wave therein for both the healthy beat and the AF beat. According to information theory, entropy or energy of the system is a significant signature of the irregularity, harmony and organizing level. In this preferred embodiment, the energy or entropy within the ROI window is utilized to characterize and diagnosis the AF severity. For example, Shannon entropy is determined according to the following formula:

$$H(P) = -\sum_{s \in S} P(s) \cdot \log P(s)$$

(S is the ROI window) and is utilized for energy integration. Additionally, the energy is determined by using time or frequency integration of the ROI atrial electrophysiological activity window.

The data representing at least one P wave signal, e.g. the healthy beat, is retrieved from storage from a data repository. The repository stores a plurality of data sets which represent at least one P wave signal associated with respective physiological characteristics. The data to be used for comparison is either automatically selected based on data input regarding the patient from which the ECG is taken or by a user through a user interface connected to the system. These characteristics may include but are not limited to at least one of age, weight, gender, sex and ethnicity, etc. and any combination thereof. The results of the comparison are provided as an output signal for presenting to a user for analysis.

The output signal may be provided to any of a data transmission device, a data recording device, an alarm generator and a display. The data transmitter 34 transmits the output signal to a network to which the system is connected. A remote unit may be connected to the network via a LAN or WAN for viewing and analysis by a user at a remote location. The data recording device or buffer 36 records the output signal generated by the integration circuit for creating a patient history. The alarm 38 receives the output signal from the integration processor and generates at least one of an audible and visual alarm in response to a determination the patient is in atrial arrhythmia such as AF. The display 40 is connected directly to the system 20 for providing a display of the cardiac signal to the user of the system.

Figure 7:
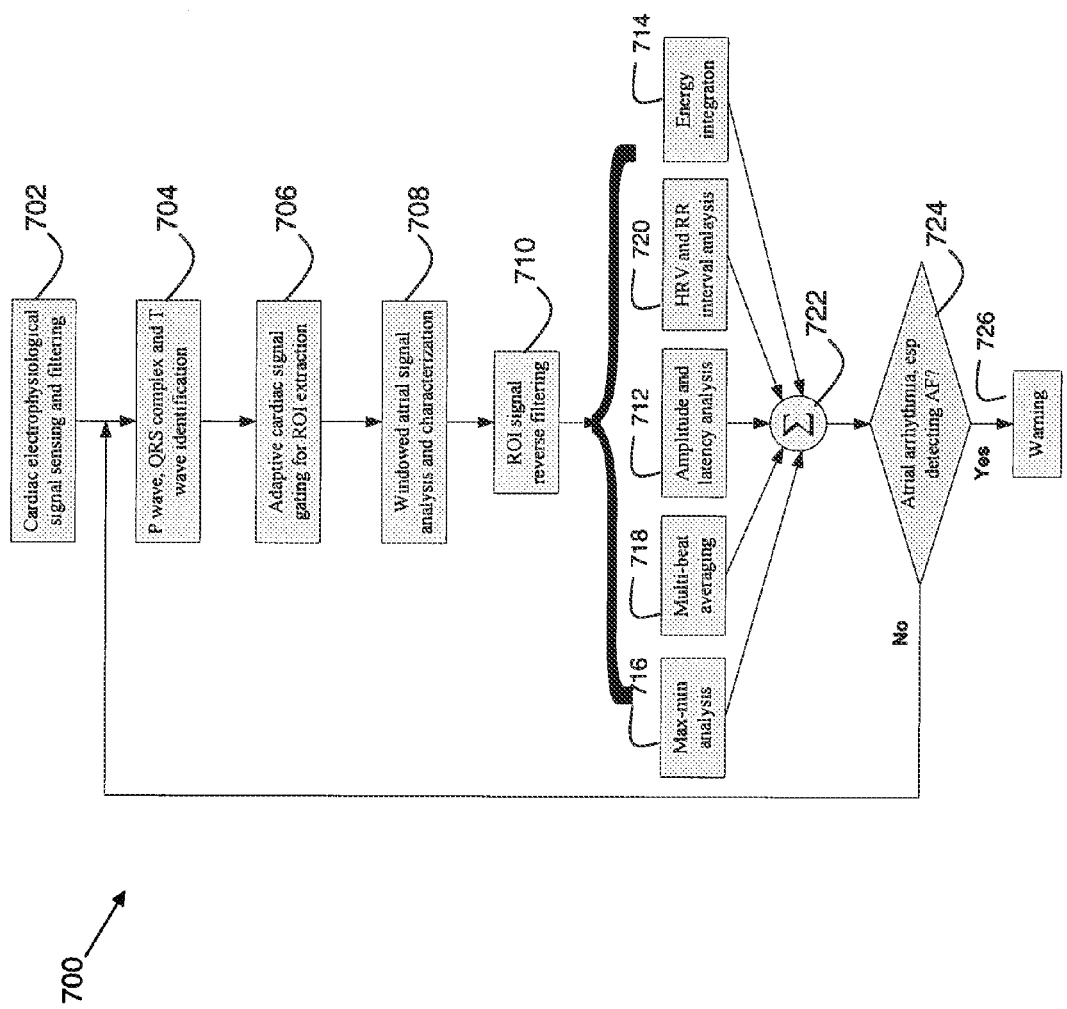
FIG. 7 is a flow diagram showing signal gating techniques and windowed analysis based methods and strategies for acquiring arterial fibrillation data, according to invention principles.

FIG. 7 is a flow chart illustrating signal gating and ROI window extraction of atrial electrophysiological activities using waveform diagrams. By using adaptive filtering and signal threshold setting as discussed above with respect to FIG. 3, the R-wave, T-wave and Q-wave is precisely identified and localized.

Compared with a known method of analysis which utilizes the whole heart beat for AF information extraction, the gating system provides more reliable and precise atrial signal portion without any distortion and artifacts from depolarization or ventricular activities. Additionally, signal gating systems according to invention principles provide a new and easy method for atrial pathology detection (P wave duration is a signature for atrial activities and the time length of the duration is utilized for pathology detection and diagnosis, such as AF, AV block, etc.) through analysis of characteristics of a P-wave within the T-Q window. Based on the atrial electrophysiological signal gating, the time duration and size of the atrial signal window (ROI) is derived. The cardiac signal data stream within the ROI is analyzed and detected characteristics of the cardiac signal data stream is compared with characteristics of a reference data stream to detect atrial arrhythmias. The analysis of the ROI may include any of averaging time duration, time variability, standard deviation, etc.

Signal gating systems are the basis of windowed cardiac signal processing and analysis. Precise and stable extractions of the ROI portion of the cardiac signal for atrial electrophysiological activities are essential to AF event detection and severity characterization. For AF analysis, the signal gating system is achieved by P wave port extraction. There are several steps for the procedure:

Step 1: Cardiac signal R-wave detection
Step 2: T-wave and Q-wave detection
Step 3: Signal gating and ROI extraction from T-wave to Q-wave FIG. 7 is a flow chart 700 showing signal gating and windowed analysis based methods and strategies for AF data acquisition, diagnosis, characterization and warning. The electrophysiological signal is sensed and filtered to remove noise therefrom in step 702. The filtered signal is then analyzed to detect and identify the P wave, QRS complex and T-wave in step 704. Adaptive signal gating and windowing is performed to extract the T-Q interval as the ROI in step 706. The atrial signal in the ROI window is analyzed and characterized in step 708. The sequence of the windowed cardiac signal analysis and characterization includes ROI signal port reverse filtering, Max-min peak analysis, etc. in step 710. The reverse filtering of the windowed ROI signals avoids the signal fluctuations and distortions from the noise and artifacts, such as R-wave. The windowed signal analysis and characterization strategies according to invention principles are utilized for atrial arrhythmia diagnosis. Amplitude and latency of P wave analysis 712 is utilized for characterizing severity and level of AF pathology and reoccurrence prediction and energy integration 714 within the ROI window is utilized to characterize and diagnosis the AF severity by comparing the atrial signal within the ROI with a reference signal and detecting a deviation of the atrial signal within the ROI from the reference signal.

Figure 8:
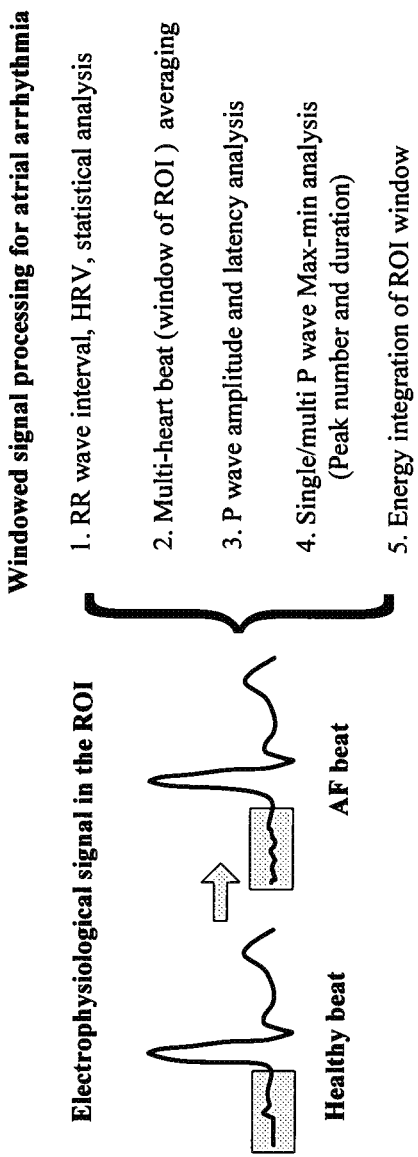
FIG. 8 shows a sequence of windowed signal processing based methods and strategies for atrial arrhythmia analysis and identification, according to invention principles.

Additionally, Max-min peak analysis as discussed in step 716 is utilized for atrial flutter (usually multi semi-P waves), multi-heart beat (window ROI) averaging as discussed in step 718 indicates AF or atrial arrhythmias and RR-wave internal and HRV analysis as discussed in step 720 is utilized for qualitative detection and analysis for the atrial arrhythmia. The Σ of step 722 represents combining the signal calculation and processing results for a comprehensive conclusion of the current cardiac electrophysiological monitoring. (The process in other embodiments may use artificial neural network, expert system, fuzzy evaluation, for example) Combining the signal calculation and processing results for analyzing atrial arrhythmia and identification discussed in step 722 is illustrated in FIG. 8. This figure illustrates the sequence of windowed signal processing based methods and strategies for atrial arrhythmia analysis and identification, especially for AF. By using signal gating systems, electrophysiological activities in atrium is extracted with ROI window and windowed signal processing is applied for analysis, detection and characterization of the atrial arrhythmias.

In the windowed signal processing system, there are independent methods which are combined and utilized:
i. RR-wave interval, HRV and statistical analysis. Rate variability is an intrinsic signal signature of the cardiac activities. Big variability indicates pathology and inharmonic changes of the tissue. It uses time interval to detect the malfunctions along a cardiac excitation pathway. For example, the shortened and prolonged excitation time (like R-wave in the depolarization and repolarization) may indicate the tissue pathology and arrhythmia. In the preferred embodiment, RR-wave internal and HRV analysis is utilized for qualitative detection and analysis for the atrial arrhythmia. More specific diagnosis and severity characterization is achieved in following methods.

ii. Multi-heart beat (window ROI) averaging. During atrial arrhythmias, especially fibrillation, the atrium falls into a disorganized inharmonic electrophysiological activity. According to the random theory, the more unorganized irregularity of the atrium, the higher degree of the AF severity heart has. Hence multi-beat averaging with the windowed ROI signal portion can reflect the severity of the atrial fibrillation is in the heart. For example the peak value of multi-beat averaging window is 50% lower than that of P wave in the healthy heart beat may definitely indicates the AF or atrial arrhythmias.

iii. P wave amplitude and latency analysis. At the early stage of atrial arrhythmia, such as AF, the pathological changes within the electrophysiological activities of P wave portion (windowed ROI signal) is not significant and may not be easily captured or detected by clinical user. This also requires extensive clinical expertise and knowledge on the atrial arrhythmias. However with the gated windowed ROI signal (P wave portion), computer based signal processing can easily capture the P wave amplitude and latency change, even to 10 uV and 10 mS. Amplitude and latency changes of the P wave is utilized as reliable and sensitive measure for atrial fibrillation detection, diagnosis and especially the severity of the AF stages.

iv. Single and multi P wave max-min analysis (peak number and duration). Different kinds of atrial arrhythmia have different symptoms and electrophysiological signal responses. Peaks and number and duration of the ROI (P wave) portion are used for arrhythmia characterization. For example, compared with normal healthy heart beats, the atrial flutter has more small peaks. Max-min (Peak and valley analysis) of the ROI portion provides additional information of the arrhythmia type and severity (un-organized degree).

v. Energy integration of ROI window. According to information theory, entropy and energy of the system is a significant signature of the irregularity, harmony and organizing level. In this preferred embodiment, the energy or entropy within the ROI window is utilized to characterize and diagnosis the AF severity.

The methods work together by combining and integrating the calculation results and each one of the processing algorithm is utilized alone for AF event detection, diagnosis and characterization. There are several methods for the analysis combination and integration, such as using artificial neural network, expert system, fuzzy evaluation, etc.

The combination of the information obtained from each analysis is used to detect Atrial arrhythmia such as AF as discussed in step 724. If Atrial arrhythmia is detected, a warning is provided to the user in step 726. Otherwise, the system continues to monitor the electrophysiological signal.

Figure 9:
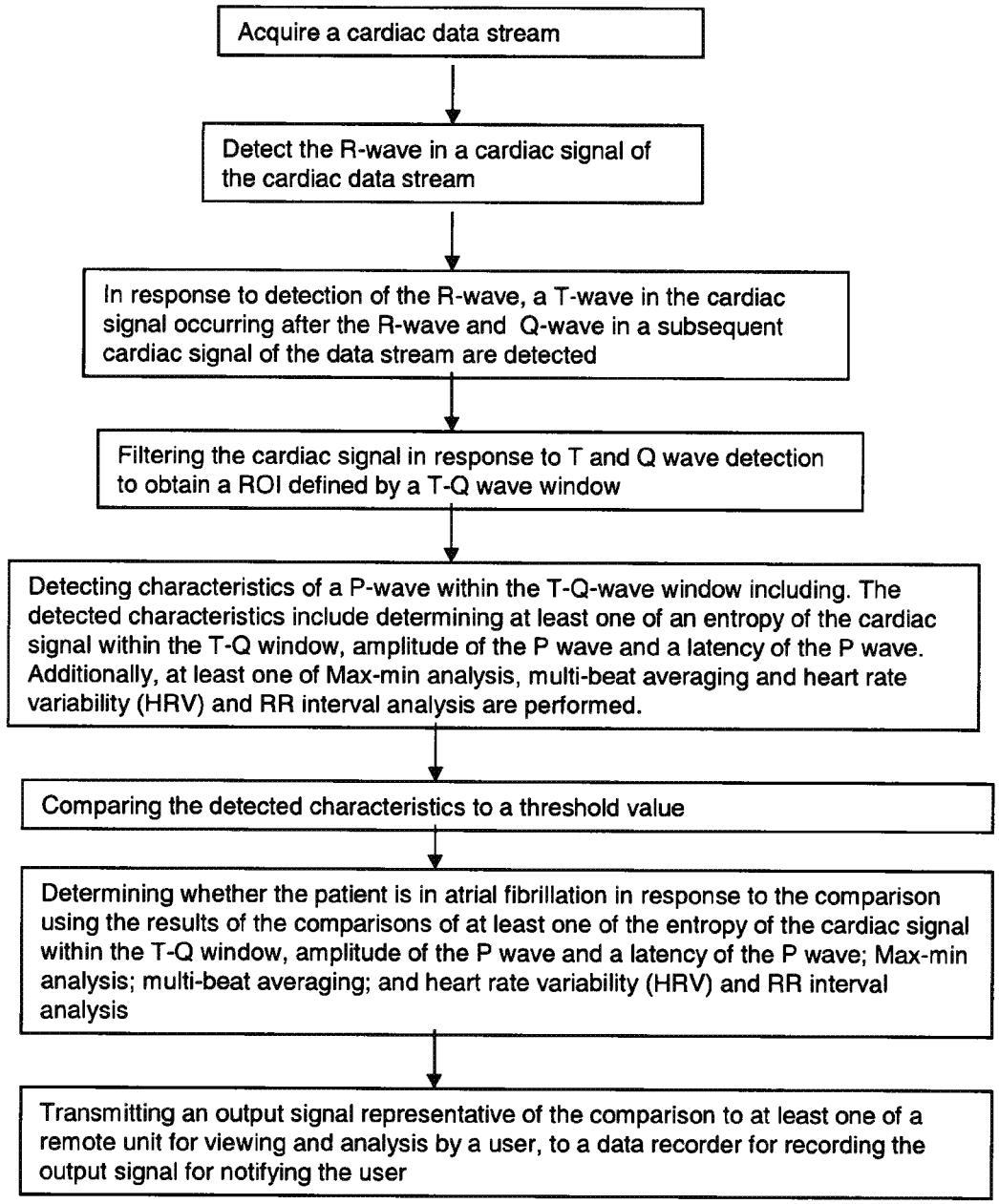
FIG. 9 is a flow diagram illustrating a method of analysis of cardiac electrophysiological signals and detection of atrial arrhythmia according to invention principles.

FIG. 9 illustrates a method of analysis of cardiac electrophysiological signals and detection of atrial arrhythmia according to invention principles. A cardiac signal data stream is acquired in step 902. The R-wave in a cardiac signal of the cardiac signal data stream is detected in step 904. In response to detection of the R-wave, a T-wave in the cardiac signal occurring after the R-wave and a Q-wave in a subsequent cardiac signal of the data stream are detected in step 906. In response to detection of the T and Q waves, the cardiac signal is filtered to obtain a ROI defined by a T-Q-wave window in step 908. Characteristics of a P-wave within the T-Q-wave window are detected in step 910. The detected characteristics include determining at least one of an entropy of the cardiac signal within the T-Q window, amplitude of the P wave and a latency of the P wave. Additionally, at least one of Max-min analysis, multi-beat averaging and heart rate variability (HRV) and RR interval analysis are performed. The detected characteristics are compared to a threshold value in step 912. A determination whether a patient is in atrial fibrillation is made in response to the comparison as in step 914. The determination is made using the results of the comparisons of at least one of the entropy of the cardiac signal within the T-Q window, amplitude of the P wave and a latency of the P wave; Max-min analysis; multi-beat averaging; and heart rate variability (HRV) and RR interval analysis. An output signal representative of the comparison is transmitted to at least one of a remote unit for viewing and analysis by a user, to a data recorder for recording the output signal for notifying the user in step 916. Determining an entropy of the signal within the T-Q wave window is performed according to:

$$H(P) = -\sum_{s \in S} P(s) \cdot \log P(s)$$

wherein s is the ROI window.

Signal gating identifies and extracts the atrial electrophysiological activities. Certain embodiments according to invention principles provide a series independent calculation (which means the calculation is utilized alone for the atrial pathology evaluation and diagnosis) and analysis methods and strategies for AF detection and characterization, such as Max-min analysis, beat averaging, amplitude/latency analysis, HRV-RR-wave analysis, Energy evaluation, etc.

Compared with normal (healthy) atrial activity, AF electrophysiological signals usually present disorders and irregularities. From a low level tissue evaluation point, AF pathological activities are a statistical combination of action potentials of the cardiac cells in atrium. During atrial arrhythmia, such as AF, the atrial cell can not work in the normal excitation sequence and most of the cells are working in chaos which will reduce the P wave power (amplitude and energy) and postpones the P wave excitation (latency) and time duration. In some cases, such as atrial flutter, the excitation is conducting in different pathways (there might be different atrial excitation rotors in atrium) which may result in several different small electrophysiological potential peaks and multi-P wave rhythms. In the atrial flutter case, the energy and morphology may be used together to characterize the pathology and severities. In some severe cases of atrial fibrillation, most tissue and cells are in random working and un-organized excitations status, the multi-window (multi-heart beat) averaging is utilized to track and capture the maximum of P wave potential for pathology detection.

The signal gating system and windowed signal processing is utilized for both surface ECG signals and intra-cardiac signals. The preferred methods and calculation is applied to both unipolar and bipolar signals for atrial fibrillation characterization.

The analysis and methods can not only be utilized for qualitative and quantitative characterization (type and severity) of the atrial arrhythmias, but be used for cardiac pathology prediction, especially for the persistent atrial fibrillation.

The methods and strategies using signal gating systems and windowed atrial electrophysiological activity analysis is modified based on the medical application, such as ROI signal portion from P wave to QRS complex, and even late cardiac potential portion analysis. The preferred methods are not limited to diagnosis and characterization of atrial fibrillation but also is used for identifying the cardiac disorders, differentiating cardiac arrhythmias, characterizing the pathological severities, and even prediction of the life-threatening events, such as ventricular arrhythmia (tachycardia and fibrillation).

The systems and processes of FIGS. 1-9 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The inventive principles involved in the system for monitoring and characterization for atrial fibrillation are applicable to other medical and non-cardiac conditions. The processes and applications may, in alternative embodiments, be located on one or more (e.g., distributed) processing devices accessing a network linking the elements of FIG. 3. Further, any of the functions and steps provided in FIGS. 1-8 may be implemented in hardware, software or a combination of both and may reside on one or more processing devices located at any location of a network linking the elements of FIG. 3 or another linked network, including the Internet.

What is claimed is:

1. A system for monitoring atrial fibrillation comprising:
a data acquisition processor for acquiring a cardiac signal data stream from a patient;
a wave detector for detecting an R-wave in a cardiac signal of the data stream, said wave detector detecting a T-wave in the cardiac signal occurring after the detected R-wave and a Q point in a successive subsequent cardiac signal of the data stream;
a filter for signal gating and extraction of data representing a Region of Interest (ROI) time window from substantially the end of the detected T-wave to the detected successive subsequent Q point;
an integration processor for detecting characteristics of a P wave signal occurring within the ROI time window, comparing a latency of the P wave comprising a time duration within the ROI time window that the P wave occurs relative to both the T-wave and the Q-wave within the ROT time window, to corresponding characteristics derived from data representing at least one P wave signal and generating an output signal in response to the comparison for use in determining if the patient is in atrial fibrillation.

2. The system as claimed in claim 1, wherein the detected characteristics include an amplitude of the P wave and an entropy of the cardiac signal.

3. The system of claim 2, wherein the entropy of the cardiac signal is determined according to:

$$H(P) = -\sum_{s \in S} P(s) \cdot \log P(s)$$

wherein s is the ROI window.

4. The system of claim 2, further comprising a processor for performing Max-min analysis; multi-beat averaging; and heart rate variability (HRV) and RR interval analysis.

5. The system of claim 4, wherein said integration processor generates the output signal in response to any combination of detecting the entropy of the cardiac signal within the T-Q window; Max-min analysis; multi-beat averaging; and heart rate variability (HRV) and RR interval analysis.

6. The system of claim 1, further including a repository for storing a plurality of data sets from which the data representing at least one P wave signal is selected.

7. The system of claim 6, wherein the data of each of the plurality of data sets represent at least one P wave signal associated with a respective physiological characteristic.

8. The system of claim 7, wherein the associated physiological characteristics include at least one of age, weight, gender, sex and ethnicity.

9. The system of claim 1, further comprising a transmitter for automatically transmitting the output signal to a remote unit for viewing and analysis by a user.

10. The system of claim 1, further comprising a buffer for recording the output signal generated by the integration processor.

11. The system of claim 1, further comprising an alarm for notifying a user in response to a determination the patient is in atrial fibrillation.

12. The system of claim 11, wherein said alarm receives the output signal from said integration processor and generates at least one of an audible and visual alarm in response to a determination the patient is in atrial fibrillation.

13. A method for detecting atrial fibrillation, said method comprising the activities of:
    acquiring a cardiac signal data stream;
    detecting an R-wave in a cardiac signal of the cardiac signal data stream;
    detecting a T-wave in the cardiac signal and a Q point in a successive subsequent cardiac signal of the data stream;
    filtering the cardiac signal to obtain a T-Q window from substantially the end of the detected T-wave to the detected successive subsequent Q point;
    detecting characteristics of a P wave within the T-Q window; and
    comparing the detected P wave characteristics including a latency of the P wave comprising a time duration within the T-Q time window that the P wave occurs relative to both the T-wave and the Q-wave within the T-Q time window, to a threshold value; and
    determining if a patient is in atrial fibrillation in response to the comparison.

14. The method as claimed in claim 13, wherein the activity of detecting characteristics includes determining an amplitude of the P wave and an entropy of the cardiac signal within the T-Q window.

15. The method as claimed in claim 13, wherein said activity of determining entropy is performed according to:

$$H(P) = -\sum_{s \in S} P(s) \cdot \log P(s)$$

wherein s is the ROI window.

16. The method as claimed in claim 13, further comprising the activity of transmitting the output signal to a remote unit for viewing and analysis by a user.

17. The method as claimed in claim 13, further comprising the activity of recording the output signal generated by the integration processor.

18. The method as claimed in claim 13, further comprising the activity of determining the patient is in atrial fibrillation in response to the comparison and notifying a user.

19. The method as claimed in claim 13, further comprising the activities of:
    performing at least one of Max-min analysis, multi-beat averaging and heart rate variability (HRV) and RR interval analysis; and
    determining if atrial fibrillation has occurred in response to both said activities of comparing and performing.

20. A method for detecting atrial fibrillation, said method comprising the activities of:
    acquiring a cardiac signal data stream;
    detecting an R-wave in a cardiac signal of the cardiac signal data stream;
    detecting a T-wave in the cardiac signal and a Q point in a successive subsequent cardiac signal of the data stream;
    filtering the cardiac signal to obtain a T-Q window from substantially the end of the detected T-wave to the detected successive subsequent Q point;
    detecting characteristics of a P wave within the T-Q window; and
    comparing the detected P wave characteristics including a latency of the P wave comprising a time duration within the T-Q time window that the P wave occurs relative to both the T-wave and the Q-wave within the T-Q time window, to a threshold value; and
    determining if a patient is in atrial fibrillation in response to the comparison.

21. The method as claimed in claim 20, further comprising the activities of:
    comparing the detected P wave characteristics including an amplitude of the P wave, to said threshold value.

* * * * *